(12) United States Patent
Han

(10) Patent No.: US 10,359,407 B2
(45) Date of Patent: Jul. 23, 2019

(54) QUALITY CONTROL MARKER AND ITS USE IN CORDYCEPS SPECIES AUTHENTICATION

(71) Applicant: Hong Kong Baptist University, Hong Kong (HK)

(72) Inventor: Quanbin Han, Hong Kong (HK)

(73) Assignee: HONG KONG BAPTIST UNIVERSITY, Hong Kong (HK)

( * ) Notice: Subject to any disclaimer, the term of this patent is extended or adjusted under 35 U.S.C. 154(b) by 198 days.

(21) Appl. No.: 15/436,797

(22) Filed: Feb. 18, 2017

(65) Prior Publication Data

US 2017/0241968 A1   Aug. 24, 2017

Related U.S. Application Data

(60) Provisional application No. 62/298,087, filed on Feb. 22, 2016.

(51) Int. Cl.
| | | |
|---|---|---|
| *G01N 33/00* | (2006.01) | |
| *G01N 33/15* | (2006.01) | |
| *B01J 20/281* | (2006.01) | |
| *G01N 33/50* | (2006.01) | |
| *G01N 30/00* | (2006.01) | |
| *G01N 30/88* | (2006.01) | |

(52) U.S. Cl.
CPC ............. *G01N 33/15* (2013.01); *G01N 30/48* (2013.01); *G01N 33/0098* (2013.01); *G01N 33/50* (2013.01); *G01N 2030/486* (2013.01); *G01N 2030/8836* (2013.01); *G01N 2333/37* (2013.01); *G01N 2400/00* (2013.01); *G01N 2496/00* (2013.01)

(58) Field of Classification Search
CPC ..... G01N 35/15; G01N 30/48; G01N 30/0098
USPC ........................................................ 73/61.53
See application file for complete search history.

(56) References Cited

U.S. PATENT DOCUMENTS

2010/0124583 A1* 5/2010 Medoff .................... A61K 8/97
426/2

* cited by examiner

*Primary Examiner* — John Fitzgerald
*Assistant Examiner* — Rodney T Frank
(74) *Attorney, Agent, or Firm* — Idea Intellectual Limited; Margaret A. Burke; Sam T. Yip

(57) ABSTRACT

The present invention relates to a quality control marker and method of using such marker in qualitative and quantitative authentication of *Cordyceps sinensis*, which is known as a Chinese medicine under the name of Dongchong Xiacao 冬蟲夏草.

8 Claims, 12 Drawing Sheets

QUALITY CONTROL MARKER AND ITS USE IN CORDYCEPS SPECIES AUTHENTICATION

CROSS REFERENCE

This application is a non-provisional application of U.S. Provisional Patent Application Ser. No. 62/298,087 filed Feb. 22, 2016, which is hereby incorporated by reference in its entirety.

FIELD OF INVENTION

The present invention relates to a quality control marker and method of using such marker in qualitative and quantitative authentication of herbal materials, in particular but not limited to *Cordyceps* species. More particularly, the present invention relates to a chemical marker and its use in quick, efficient and low-cost authentication of *Cordyceps sinensis*, which is well-known as an expensive Chinese medicine under the name of Dongchong Xiacao (冬蟲夏草).

BACKGROUND OF INVENTION

The authentication of *Cordyceps sinensis* remains a challenge. Varied methods, including microscopic, chemical and DNA approaches, have been studied, but are far from satisfactory. The conventional methods such as microscopic examination depends heavily on the experience of botanical experts and also involves subjective judgement. DNA barcoding has been studied by many scientists, but fails to be practical due to its high-cost and complicated operation. Some chemical efforts have been made, e.g. thin layer chromatography (TLC) analysis. But these chemical methods are not efficient in distinguishing *Cordyceps sinensis* from other *Cordyceps* species. More importantly, no method is able to quantitatively analyze the quality of *Cordyceps sinensis* due to lack of a proper chemical marker.

Thus, there still exists a need for a quality control and authentication method of *Cordyceps sinensis* that: 1) is rapid and low-cost; 2) has a mechanism that is easy-to-understand; 3) is simple; 4) is repeatable and reproducible in a satisfactory manner; 5) is practicable for both qualitative and quantitative analysis; 6) is reliable with a large number of sample batches, and 7) is practical for commercial application.

Citation or identification of any reference in this section or any other sections of this application shall not be construed as an admission that such reference is available as prior art for the present application.

SUMMARY OF THE INVENTION

In accordance with a first aspect of the present invention, there is provided a method for authenticating a sample of carbohydrate-containing herbal material, comprising providing a chemical fingerprint of one or more carbohydrates in the sample based on molecular weight distribution; identifying a dominant polysaccharide component of the carbohydrates in the sample; separating the dominant polysaccharide components; and developing a chemical marker to authenticate the herbal material.

In a first aspect of the present invention there is provided a method for authenticating a sample of herbal material from the *Cordyceps* species, comprising:

a. providing a chemical fingerprint of one or more carbohydrates in the sample based on molecular distribution pattern of water extract from said sample;
b. identifying a dominant component of the carbohydrates in the sample, the sample having an amount of polysaccharides, where the dominant polysaccharide component is the component of the sample having a largest amount of polysaccharides in said sample;
c. separating the dominant polysaccharide component; and
d. authenticating a sample of herbal material using the separated dominant polysaccharide component.

In a first embodiment of the first aspect of the present invention there is provided a method for authenticating a sample of herbal material from the *Cordyceps* species wherein the step of providing the chemical fingerprint includes performing size exclusion chromatography.

In a second embodiment of the first aspect of the present invention there is provided a method for authenticating a sample of herbal material from the *Cordyceps* species wherein the size exclusion chromatography is a high performance gel permeation chromatography.

In a third embodiment of the first aspect of the present invention there is provided a method for authenticating a sample of herbal material from the *Cordyceps* species wherein authenticating a sample of herbal material using the separated dominant polysaccharide component is conducted by analyzing the dominant polysaccharide component after the step of providing a chemical fingerprint by a high performance gel permeation chromatography wherein said dominant polysaccharide component is a majority in a macromolecule range of the water extract from said sample.

In a fourth embodiment of the first aspect of the present invention there is provided a method for authenticating a sample of herbal material from the *Cordyceps* species wherein the macromolecule range is in a range constituting a molecule with a retention time between 20-25 min which further corresponds to 200K-2560K of pullulan series, or 250K-1200K of dextran series.

In a fifth embodiment of the first aspect of the present invention there is provided a method for authenticating a sample of herbal material from the *Cordyceps* species wherein the separated dominant polysaccharide component is bioactive.

In a sixth embodiment of the first aspect of the present invention there is provided a method for authenticating a sample of herbal material from the *Cordyceps* species wherein said *Cordyceps* species comprises *Cordyceps sinensis*.

In a second aspect of the present invention there is provided a method of preparing a chemical marker for use in qualitative and quantitative authentication of a sample of herbal material from the *Cordyceps* species, comprising:

a. providing a chemical fingerprint of one or more carbohydrates in the sample based on a molecular distribution pattern of water extract from said sample;
b. identifying a dominant polysaccharide component of the carbohydrates in the sample, the sample having an amount of polysaccharides, where the dominant polysaccharide component is the component of the sample having a largest amount of polysaccharides in said sample;
c. separating the dominant polysaccharide component to form a separated dominant polysaccharide component; and d. analyzing the separated dominant polysaccharide component as the chemical marker for use in qualitative and quantitative authentication of an herbal sample.

In a first embodiment of the second aspect of the present invention there is provided a method of preparing a chemical marker for use in qualitative and quantitative authentication of a sample of herbal material from the *Cordyceps* species wherein providing the chemical fingerprint includes performing a size exclusion chromatography.

In a second embodiment of the second aspect of the present invention there is provided a method of preparing a chemical marker for use in qualitative and quantitative authentication of a sample of herbal material from the *Cordyceps* species wherein the size exclusion chromatography is a high performance gel permeation chromatography.

In a third embodiment of the second aspect of the present invention there is provided a method of preparing a chemical marker for use in qualitative and quantitative authentication of a sample of herbal material from the *Cordyceps* species wherein authenticating a sample of herbal material using the separated dominant polysaccharide component is conducted by analyzing the dominant polysaccharide component after providing a chemical fingerprint by a high performance gel permeation chromatography wherein said dominant polysaccharide component is a majority in a macromolecule range of the water extract from said sample.

In a fourth embodiment of the second aspect of the present invention there is provided a method of preparing a chemical marker for use in qualitative and quantitative authentication of a sample of herbal material from the *Cordyceps* species wherein the macromolecule range is in a range constituting a molecule with a retention time between 20-25 min which further corresponds to 200K-2560K of pullulan series, or 250K-1200K of dextran series.

In a fifth embodiment of the second aspect of the present invention there is provided a method of preparing a chemical marker for use in qualitative and quantitative authentication of a sample of herbal material from the *Cordyceps* species wherein the separated dominant polysaccharide component is bioactive.

In a sixth embodiment of the second aspect of the present invention there is provided a method of preparing a chemical marker for use in qualitative and quantitative authentication of a sample of herbal material from the *Cordyceps* species wherein said *Cordyceps* species comprises *Cordyceps sinensis*.

Throughout this specification and claims, unless the context requires otherwise, the word "include" or "comprise" or variations such as "includes" or "comprises" or "comprising", will be understood to imply the inclusion of a stated integer or group of integers but not the exclusion of any other integer or group of integers. It is also noted that in this disclosure and particularly in the claims and/or paragraphs, terms such as "included", "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE PREFERRED EMBODIMENTS

High performance gel permeation chromatography (HPGPC), a type of size exclusion chromatography that separates analytes on the basis of molecular size, is designed for analytical and preparative separation of synthesized water-soluble polymers, oligomers and biological substances such as polysaccharides, nucleic acids, proteins, peptides, etc. In the research on herbal materials, HPGPC is widely employed for homogeneity and molecular weight determination of purified polysaccharides or oligosaccharides by qualitatively characterizing peak symmetry and calculating with established retention time-molecular weight standard curve, respectively.

Figure 1A:
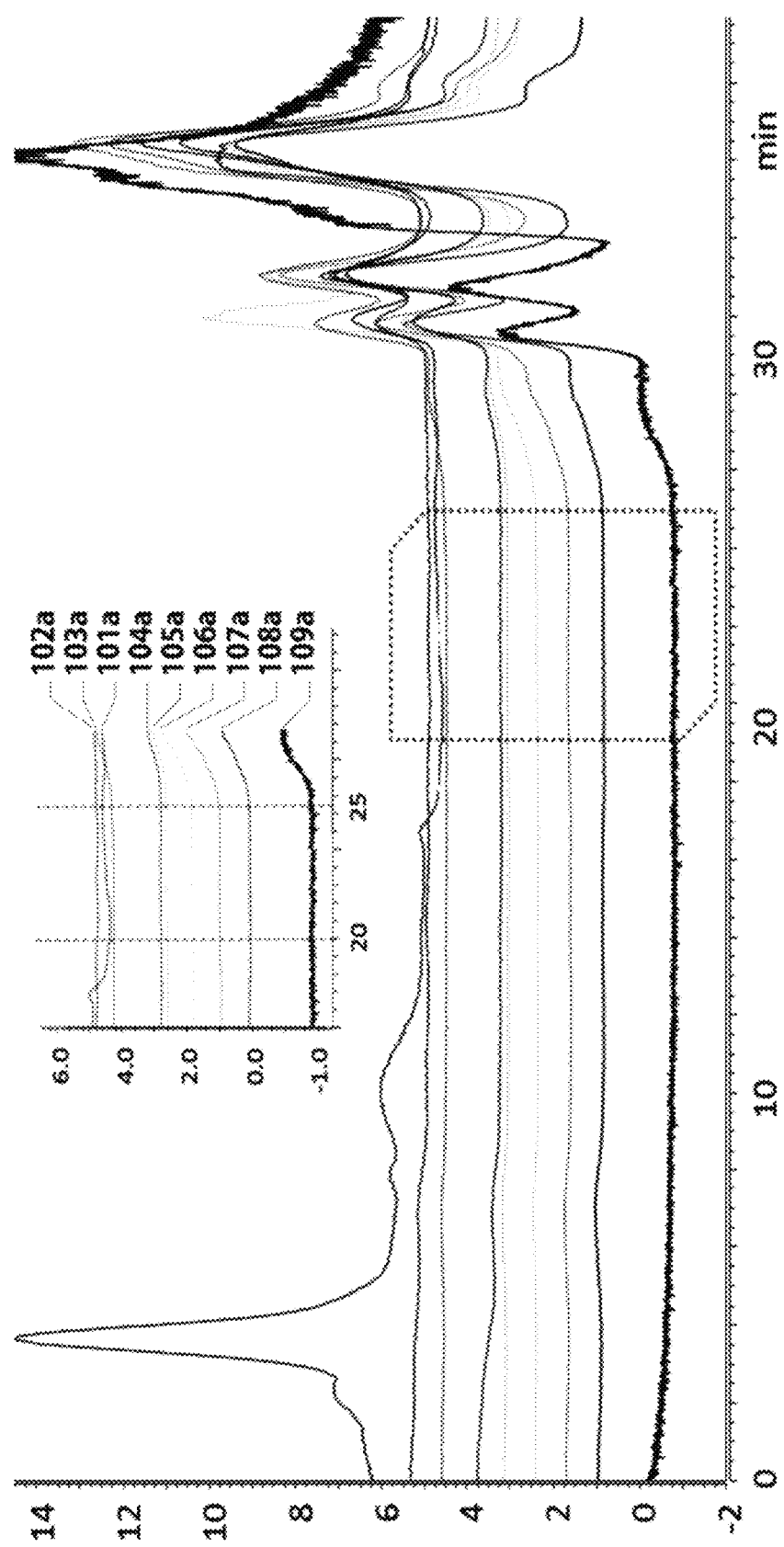
FIG. 1A shows high performance gel permeation chromatography (HPGPC) analysis of authentic samples of *Codyceps sinense*: stoma.
Figure 1B:
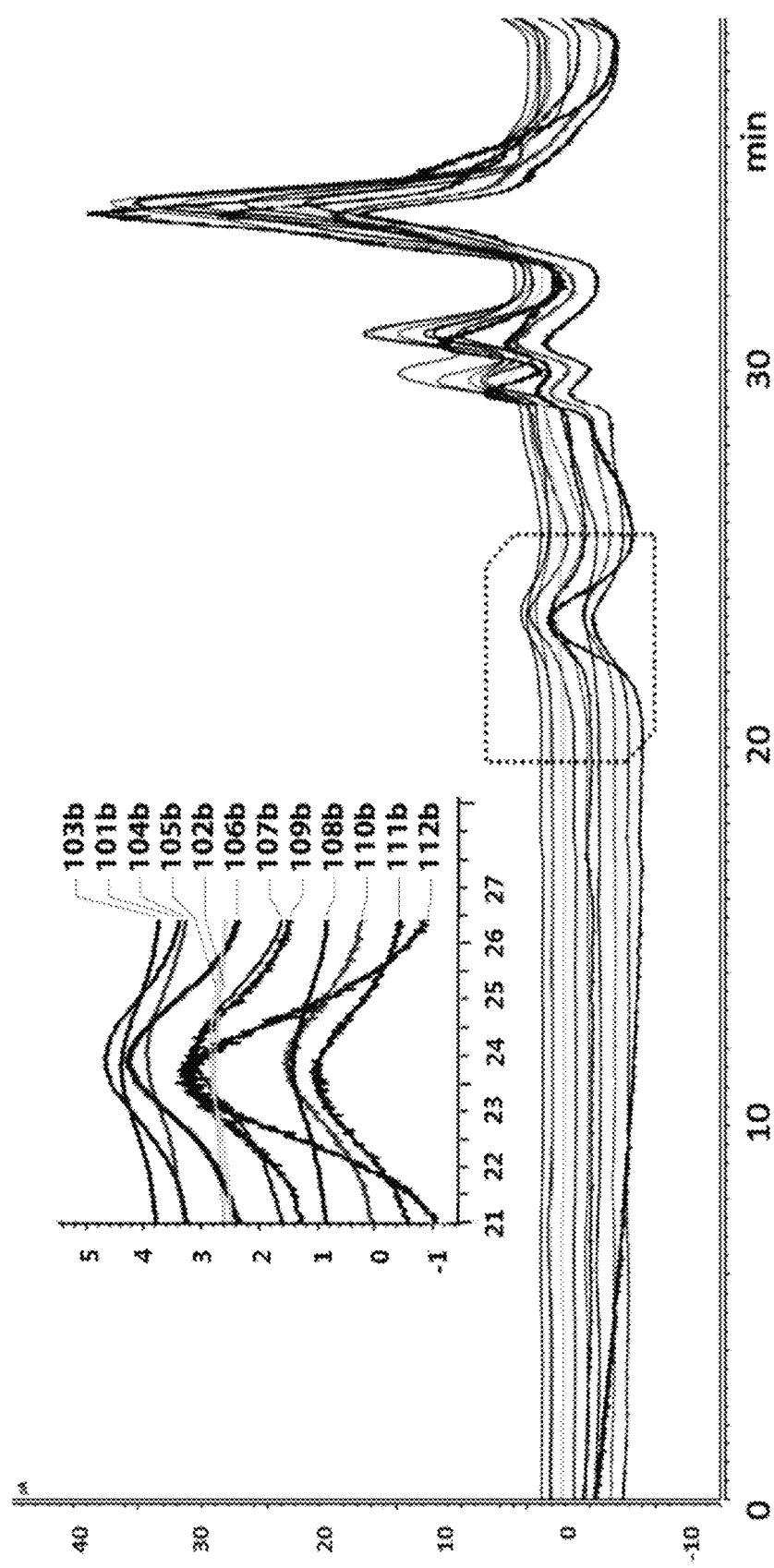
FIG. 1B shows HPGPC analysis of authentic samples of *Codyceps sinense*: caterpillar.
Figure 2A:
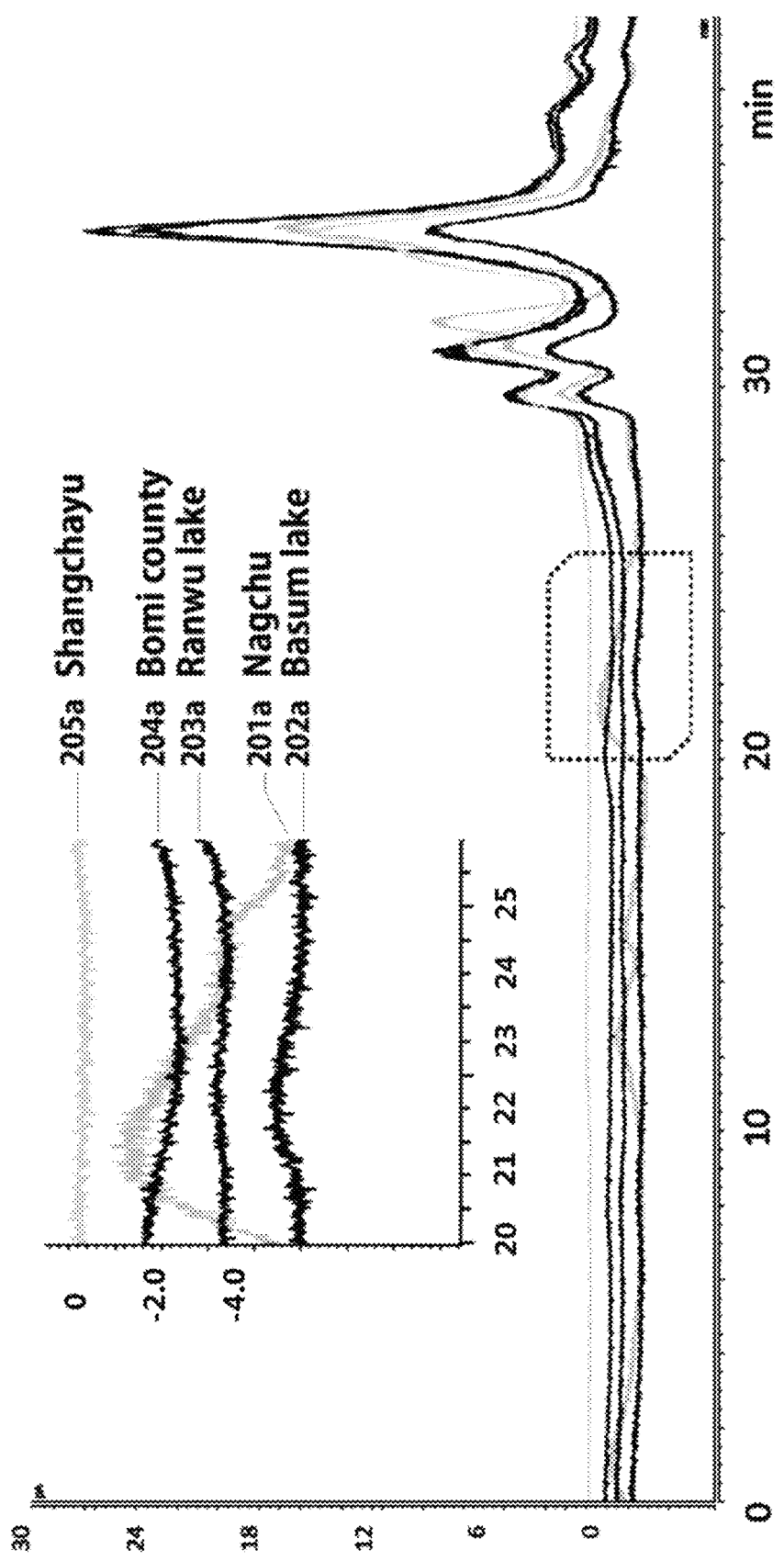
FIG. 2A shows HPGPC analysis of samples of *Codyceps sinense* from different origins: stoma.
Figure 2B:
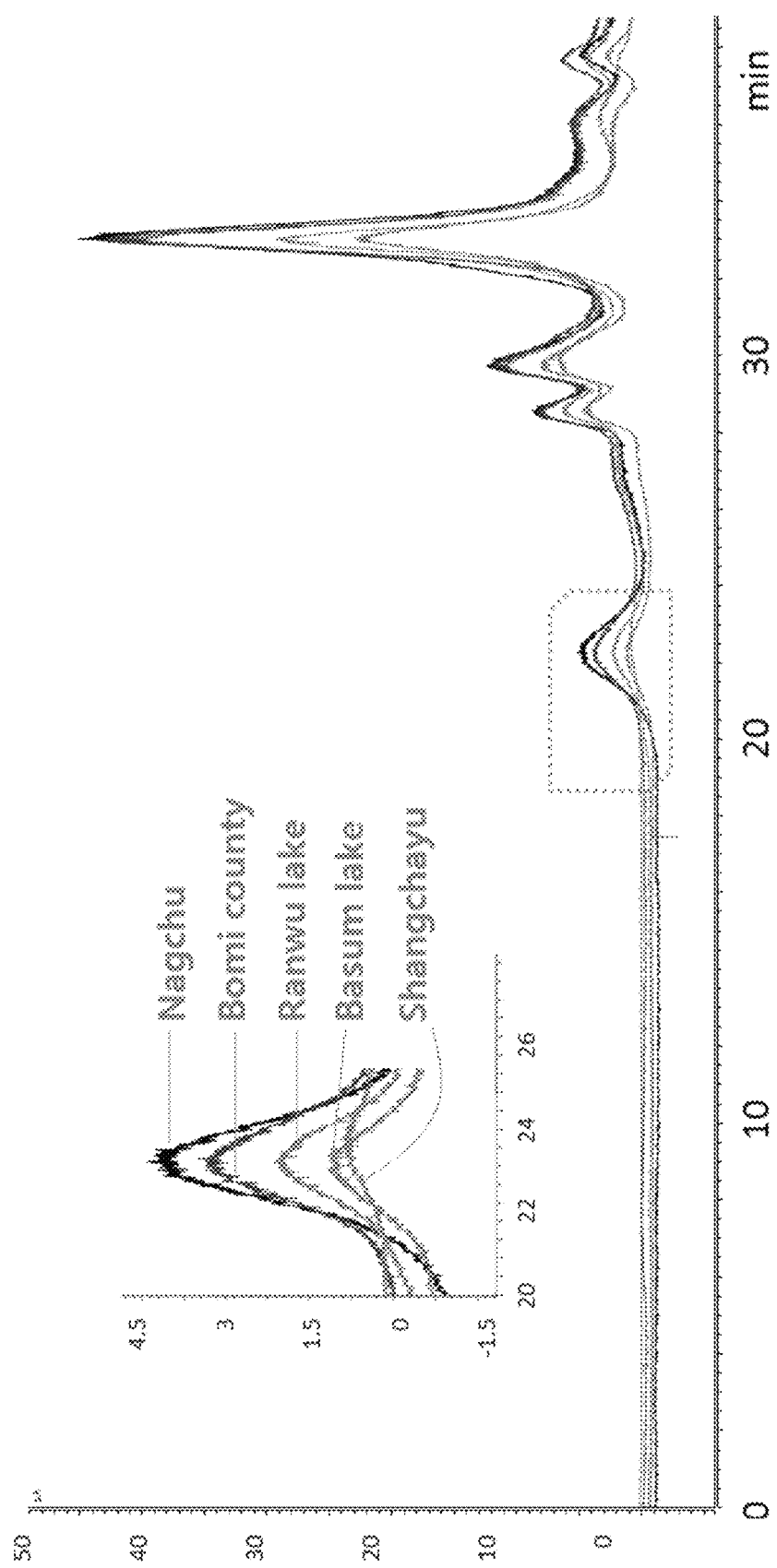
FIG. 2B shows HPGPC analysis of samples of *Codyceps sinense* from different origins: caterpillar.
Figure 3:
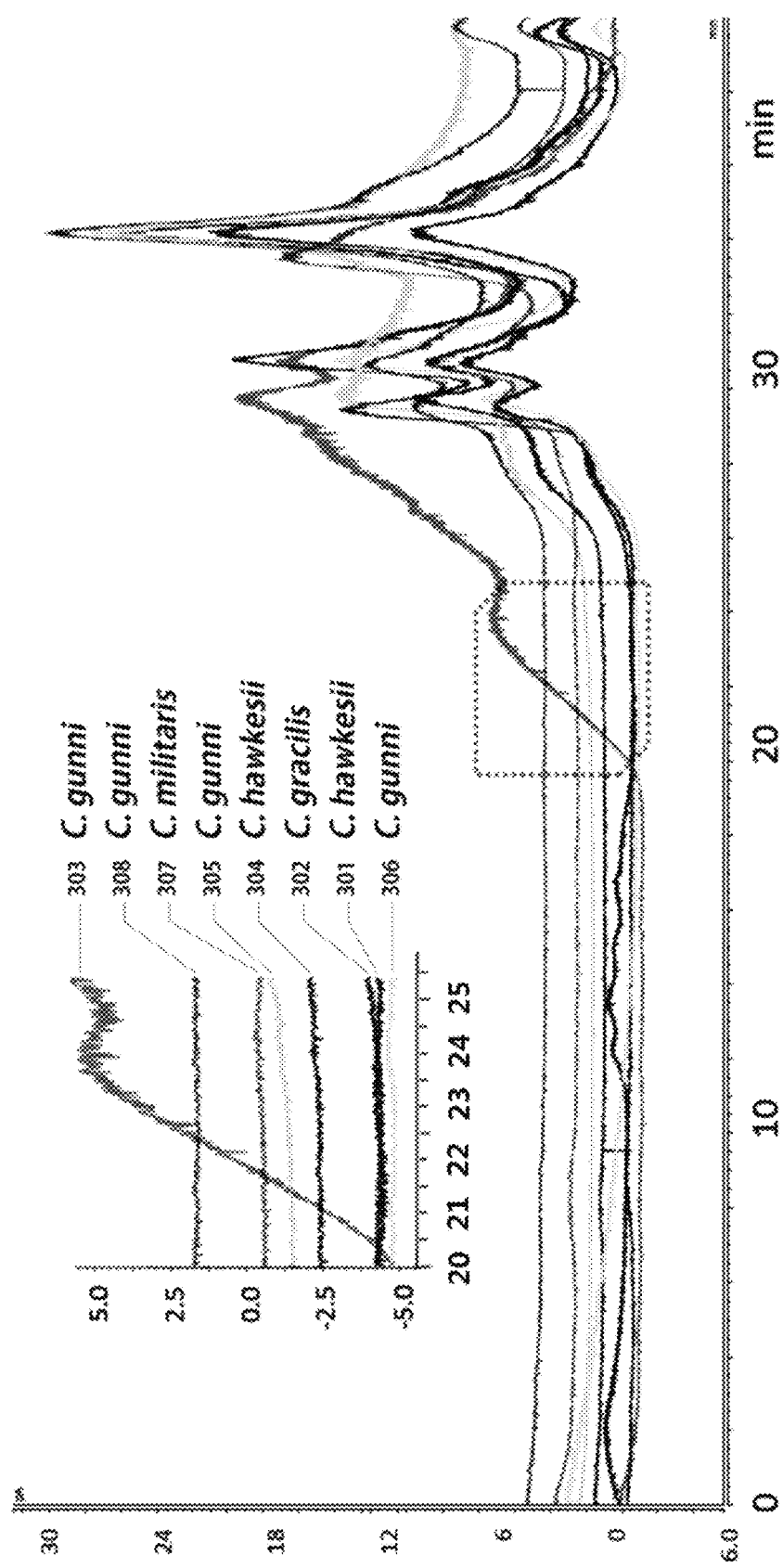
FIG. 3 shows HPGPC analysis of the caterpillar part of other *Codyceps* species: *C. hawkesii*; *C. gracilis*; *C. gunni*; *C. hawkesii*; *C. gunni*; *C. gunni*; *C. milaaris*; Lowland *Cordyceps*.
Figure 4:
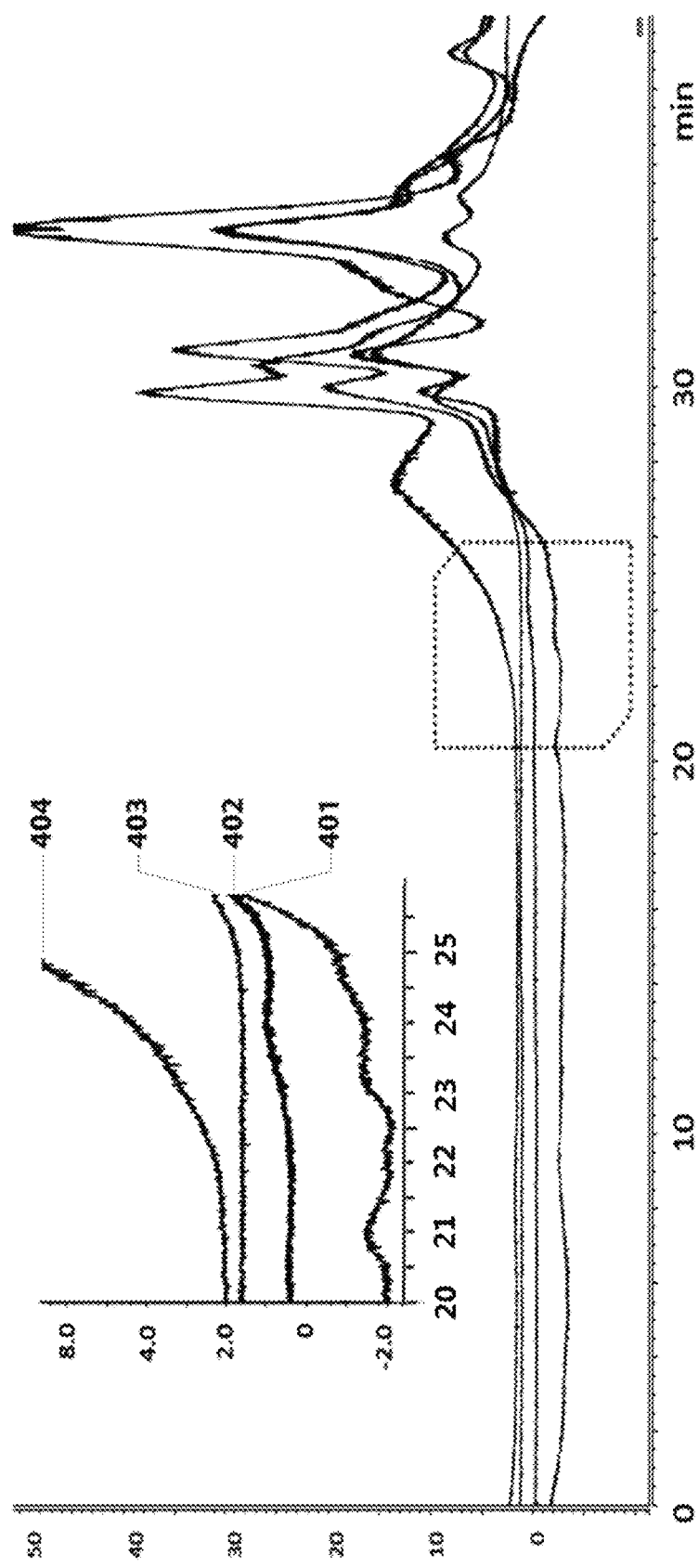
FIG. 4 shows HPGPC analysis of the caterpillar part of fake samples of *Codyceps sinense*.
Figure 5:
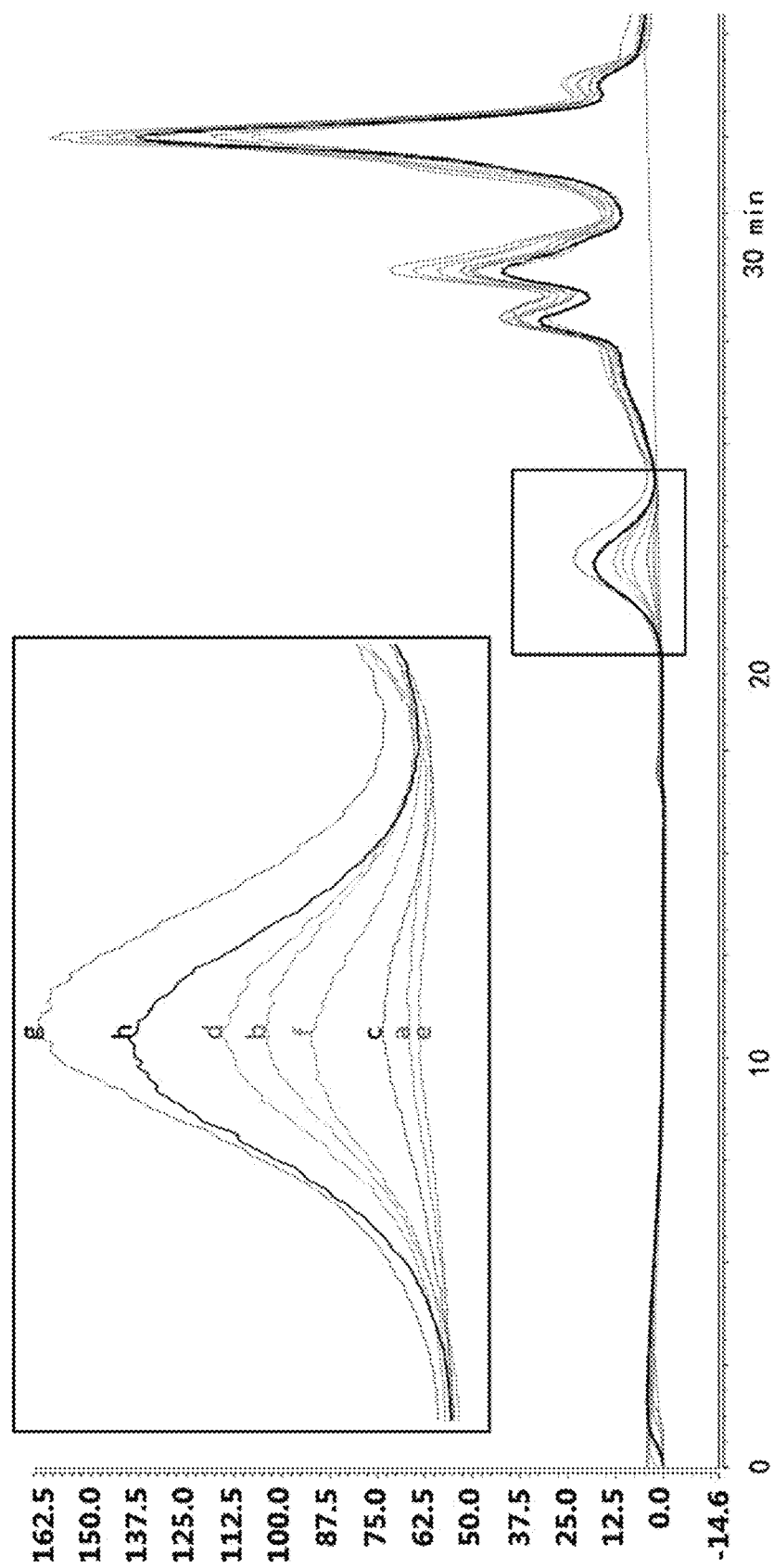
FIG. 5 shows the use of the QC marker in the quality analysis of the caterpillar part of *Cordyceps sinense* samples.
Figure 6:
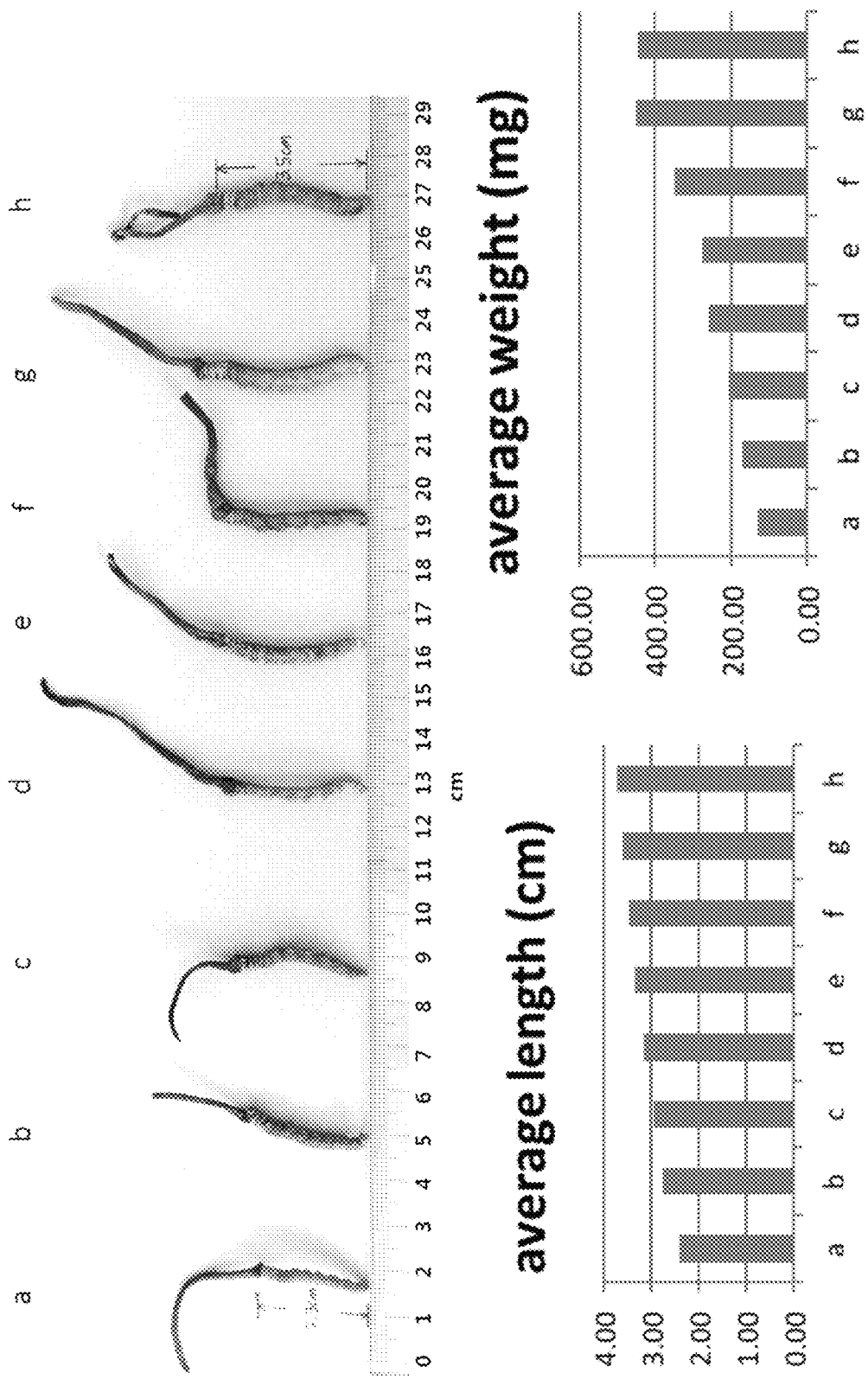
FIG. 6 shows the *Cordyceps sinensis* samples used in FIG. 5.
Figure 7A:
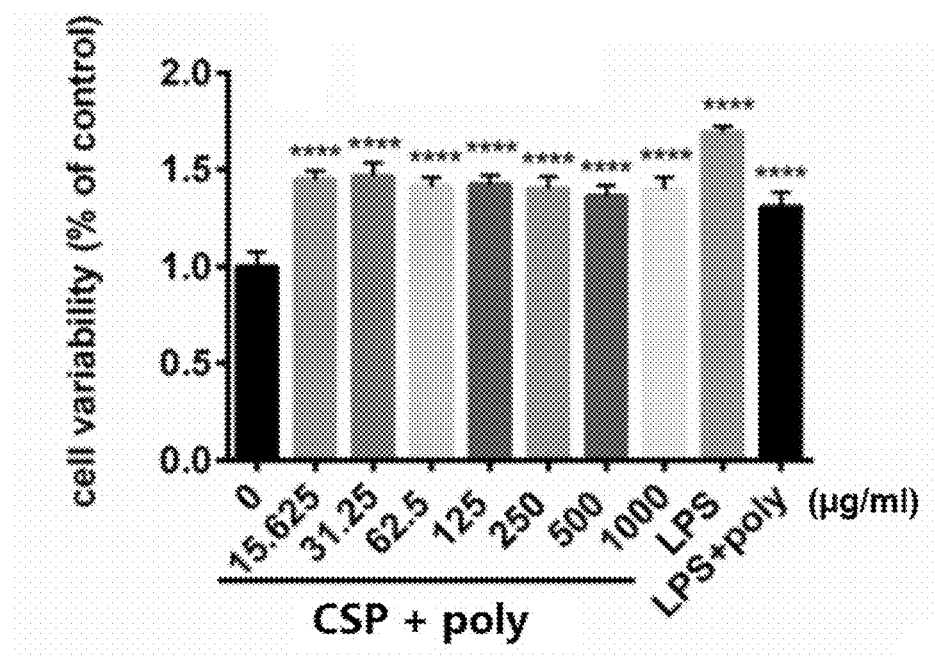
FIG. 7A shows CSP is able to induce the proliferation of RAW264.7 cells.
Figure 7B:
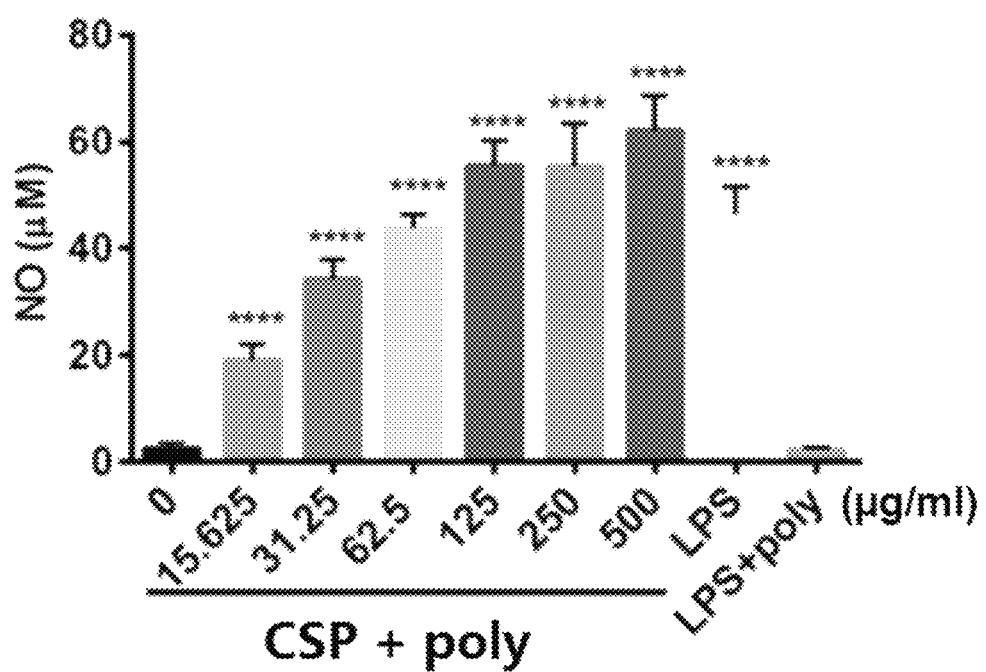
FIG. 7B shows CSP is able to enhance the production of nitric oxide in RAW 264.7 cells in a dose-dependent manner.
Figure 7C:
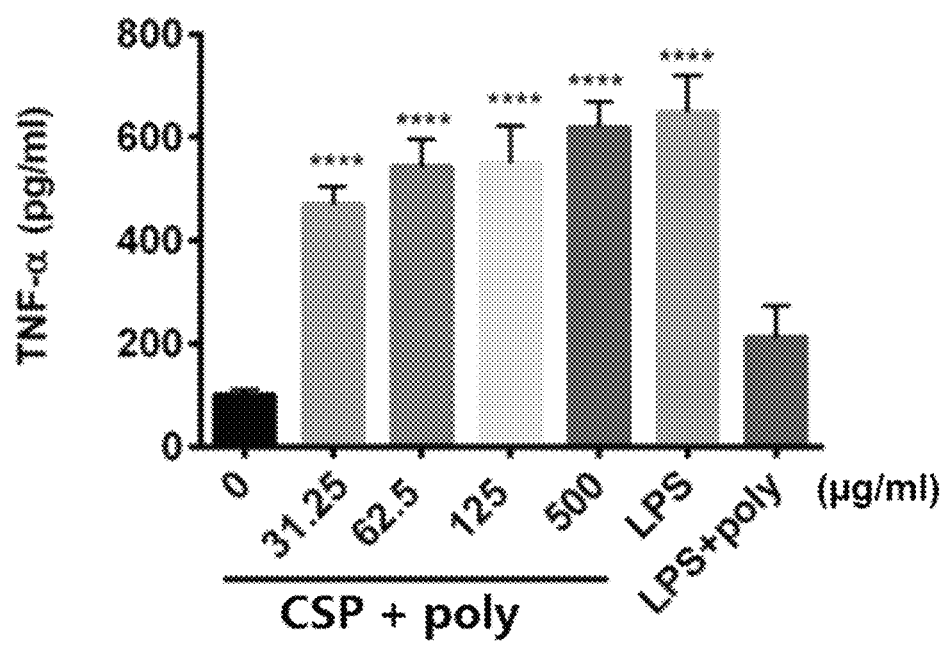
FIG. 7C shows CSP is able to enhance the secretion of TNF-$\alpha$ in RAW 264.7 cells in a dose-dependent manner.
Figure 7D:
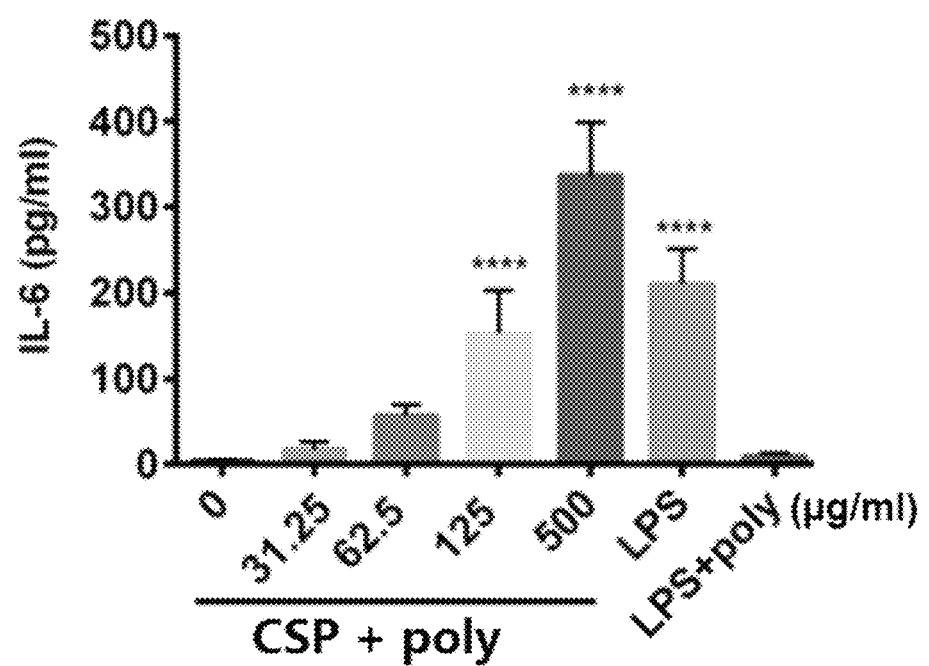
FIG. 7D shows CSP is able to enhance the secretion of IL-6 in RAW 264.7 cells in a dose-dependent manner.

In an embodiment of the present invention, taking *Cordyceps sinensis* as a model herb, a novel and rapid HPGPC based method was developed for quality control of carbohydrates in herbal materials. The molecular distribution pattern of the water extract of the polysaccharides from a few authentic *Cordyceps sinensis* samples was compared using size exclusion chromatography, which is Gel Permeation Chromatography (GPC). As illustrated in FIG. 1, these samples exhibited highly identical GPC patterns, especially, and only the caterpillar part (FIG. 1B), not the stroma part (FIG. 1A), contain one polysaccharide fraction as the majority in the macromolecule range (retention time: 20-25 min, corresponding to 200K-2560K of pullulan series, or 250K-1200K of dextran series) of the water extracts. Furthermore, commercial samples collected in the market exhibited similar GPC pattern (FIGS. 2A and 2B), and great variation in the content of this polysaccharide marker was also observed (FIG. 2B). Neither other *Cordyceps* species (FIG. 3) nor fake samples (FIG. 4) contain this polysaccharide marker, which shall be identified herein as CSP. The use of this quality control (QC) marker in authentication of *Cordyceps sinensis* is therefore established. The QC marker is further isolated and used as a reference chemical in GPC quantitative analysis, which enables evaluation of not only true/false authentication but also the quality of *Cordyceps sinensis* samples. Based on FIGS. 5 and 6, the contents of this QC marker in two of the most expensive samples g and h (with larger average weight/length) are far higher than those in the cheaper samples a and c (with smaller average weight/length), as indicated by the larger peak area. Since this marker showed immunomodulating effects on RAW264.7 cells, the amount of the QC marker present denotes the higher quality of the herbal product.

This invention may be widely applied for qualitative and quantitative authentication of *Cordyceps sinensis*. Furthermore, the present invention presents several advantages: 1) it is rapid since only two hours are need for one single analysis; 2) it is low-cost because no special reagent or instrument is required; 3) the mechanism is easy-to-understand; 4) the operation is as simple as normal HPLC analysis; 4) the repeatability and reproducibility are satisfactory; 5) it is practicable for both qualitative and quantitative analysis; 6) it is reliable with large number of sample batches, and therefore 7) it is practical for commercial application.

The present invention may be provided as a kit which includes the polysaccharide marker, a HPGPC column, and software for data analysis. The kit may be commercially provided to users to do the quality control of *Cordyceps* samples in laboratory. Therefore, the variations caused by HPGPC columns and method of data analysis will be minimized. Other possible variations are mainly from operator's operation which is normally minimized by certificated laboratory operators as other analytical techniques.

In yet another embodiment of the present invention, it is provided that the identified marker for *Cordyceps sinensis*—the CSP, is also bioactive and similar with the positive control lipopolysaccharide (LPS), CSP is able to induce the proliferation of RAW264.7 cells; and to enhance the production of nitric oxide and secretion of TNF-α, and IL-6 in RAW 264.7 cells in a dose dependent manner, as shown in FIGS. 7A to 7D. The effect of LPS was suppressed by polymyxin B, but polymyxin B did not inhibit CSP's effect.

Cell Viability Assay

The viability of RAW264.7 cells was measured using MTT assay. Briefly, RAW264.7 cells ($5 \times 10^3$ cells/well) were plated in 96-well microplates overnight and then treated with serial concentrations (15.625-1000 μg/ml) of CSP for 24 hours, respectively. Equal volume of medium was used as vehicle control. After treatment, cells were stained with MTT at a final concentration of 0.5 mg/mL in PBS (pH 7.4) for another 4 hours in dark and then the medium was discarded. The formazan crystals present in cells were dissolved by dimethyl sulfoxide. The absorbance was read at 570 nm in a Benchmark Plus microplate reader (Bio-Rad, Richmond, Calif.). The results were expressed as a ratio of absorbance values of treatment to vehicle control cells.

Measurement of Nitric Oxide (NO)

NO production was monitored by assessment of nitrite accumulation. Briefly, RAW264.7 cells ($1 \times 10^5$ cells/well) were seeded in 96-well plates overnight, and then stimulated with CSP (15.625-500 μg/ml) or LPS (100 ng/mL) for 24 hours, and LPS treatment was used as a positive control. After treatment, 100 μL of supernatants were mixed with an equal volume of Griess reagent (modified) in a 96-well plate at room temperature for 15 minutes. The optical density was determined at 540 nm on Benchmark Plus microplate reader (Bio-Rad, Richmond, Calif.). Nitrite production was determined by comparing the optical density with the standard curve obtained with $NaNO_2$. Polymyxin B (poly, 10 μg/ml) was added as LPS inhibitor to exclude LPS's influence.

ELISA for Quantitative Analysis of Cytokines

RAW264.7 cells ($1 \times 10^4$ cells/well) were seeded in 96-well plates overnight and then exposed to CSP (31.25-500 μg/ml) and LPS (100 ng/mL) for 24 hours. The cell supernatants were collected by centrifugation at 1,000×g for 10 minutes. The amount (pg/mL) of IL-6 and TNF-α secretion in culture supernatants were determined in duplicate by using an ELISA kit according to the manufacturer's instructions. Polymyxin B (poly, 10 μg/ml) was added as LPS inhibitor to exclude LPS's influence.

In a further embodiment of the present invention, it is determined that the sugar composition of CSP is determined to be mannose/glucose/galactose at a ratio of 2:6:1.

If desired, the different functions discussed herein may be performed in a different order and/or concurrently with each other. Furthermore, if desired, one or more of the above-described functions may be optional or may be combined; this includes the processes recited in the claims which are part of the overall invention and are not to be considered as discrete steps.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Those skilled in the art will appreciate that the invention described herein is susceptible to variations and modifications other than those specifically described.

INDUSTRIAL APPLICATION

The present invention relates to a quality control marker and method of using such marker in qualitative and quantitative authentication of herbal materials, in particular but not limited to *Cordyceps* species. More particularly, the present invention relates to a chemical marker and its use in quick, efficient and low-cost authentication of *Cordyceps sinensis*, which is well-known as an expensive Chinese medicine under the name of Dongchong Xiacao (冬蟲夏草).

What is claimed is:

1. A method for authenticating a sample of herbal material from the *Cordyceps* species, comprising:

providing a chemical fingerprint of one or more carbohydrates in the sample by size exclusion chromatography based on a molecular distribution pattern of water extract from said sample;

identifying a dominant polysaccharide component of the carbohydrates in the sample, the sample having an amount of polysaccharides, where the dominant polysaccharide component is the component of the sample having a largest amount of polysaccharides in said sample;

separating the dominant polysaccharide component; and authenticating a sample of herbal material using the separated dominant polysaccharide component as a chemical marker for *Cordyceps* species, wherein said authenticating step comprises analyzing said separated dominant polysaccharide component and the sample of herbal material is authenticated to be *Cordyceps* species if the separated dominant polysaccharide component is a majority in a macromolecule range of the water extract from said sample and wherein the macromolecule range is in a range constituting a molecule with a retention time between 20-25 min which corresponds to 200K-2560K of pullulan series, or 250K-1200K of dextran series.

2. The method according to claim 1, wherein the size exclusion chromatography is a high performance gel permeation chromatography.

3. The method according to claim 1, wherein the separated dominant polysaccharide component is bioactive.

4. The method according to claim 1, wherein said *Cordyceps* species comprises *Cordyceps sinensis*.

5. A method of preparing a chemical marker for use in qualitative and quantitative authentication of a sample of herbal material from the *Cordyceps* species, comprising:

providing a chemical fingerprint of one or more carbohydrates in the sample by size exclusion chromatography based on a molecular distribution pattern of water extract from said sample;

identifying a dominant polysaccharide component of the carbohydrates in the sample, the sample having an amount of polysaccharides, where the dominant polysaccharide component is the component of the sample having a largest amount of polysaccharides in said sample;

separating the dominant polysaccharide component to form a separated dominant polysaccharide component; and analyzing the separated dominant polysaccharide component as a chemical marker for use in qualitative and quantitative authentication of an herbal sample, wherein said separated dominant polysaccharide component is a majority in a macromolecule range of the water extract from said sample and wherein the macromolecule range is in a range constituting a molecule with a retention time between 20-25 min which corresponds to 200K-2560K of pullulan series, or 250K-1200K of dextran series.

6. The method according to claim 5, wherein the size exclusion chromatography is a high performance gel permeation chromatography.

7. The method according to claim 5, wherein the separated dominant polysaccharide component is bioactive.

8. The method according to claim 5, wherein said *Cordyceps* species comprises *Cordyceps sinensis*.

* * * * *